United States Patent [19]

Drent

[11] Patent Number: 5,281,744
[45] Date of Patent: Jan. 25, 1994

[54] PROCESS FOR THE PREPARATION OF NITRILES

[75] Inventor: Eit Drent, Amsterdam, Netherlands

[73] Assignee: Shell Oil Company, Houston, Tex.

[21] Appl. No.: 19,740

[22] Filed: Feb. 19, 1993

[30] Foreign Application Priority Data

Mar. 2, 1992 [EP] European Pat. Off. ........ 92200604.4

[51] Int. Cl.$^5$ ............................................. C07C 253/00
[52] U.S. Cl. ...................................... 558/314; 558/353
[58] Field of Search ................................. 558/353, 314

[56] References Cited

U.S. PATENT DOCUMENTS

| | | | |
|---|---|---|---|
| 2,417,024 | 3/1947 | Tuerck et al. | 558/314 |
| 2,820,059 | 1/1958 | Hasek et al. | 558/353 X |
| 2,956,977 | 10/1960 | Caldwell et al. | 558/353 X |
| 3,006,948 | 10/1961 | Happel et al. | 558/314 |
| 3,010,994 | 11/1961 | Iwanaga et al. | 558/353 X |
| 3,125,595 | 3/1964 | Brady et al. | 558/353 |
| 3,210,400 | 10/1965 | Brakebill et al. | 558/353 |
| 3,466,317 | 9/1969 | Kuper | 558/353 |
| 4,235,807 | 11/1980 | Fuhlhage | 558/314 |
| 4,344,896 | 8/1982 | Kurkov | 558/353 |
| 4,456,562 | 6/1984 | Tamura et al. | 558/314 |
| 4,808,746 | 2/1989 | Nishimura et al. | 558/314 |

FOREIGN PATENT DOCUMENTS 240848 7/1959 Netherlands.

*Primary Examiner*—Joseph Paul Brust

[57] ABSTRACT

A process for the preparation of nitriles in which an ethylenically unsaturated compound is reacted with carbon monoxide, a hydrogen source and hydroxylamine or a hydroxylamine salt in the presence of a catalyst system comprising one or more Group VIII metals.

6 Claims, No Drawings

PROCESS FOR THE PREPARATION OF NITRILES

FIELD OF THE INVENTION

The invention relates to a process for the preparation of nitriles, many of which may be commercially used directly, or after having been first converted into other products, such as primary amines.

BACKGROUND OF THE INVENTION

It is known that nitriles are formed by addition of HCN to an unsaturated carbon-carbon bond, e.g. the double bond of an olefin. However, in view of the risks involved in handling this highly toxic chemical, this addition method is considered unsuitable for large scale operation. Hence various attempts have been made to develop a method for producing nitriles whereby the use of HCN is avoided.

From U.S. Pat. No. 4,456,562 a process for producing nitriles is known whereby a compound of the formula R—CHO is reacted with a hydroxylamine-inorganic salt. In the event that R represents an aromatic group, the nitrile is directly produced whereas compounds in which R represents an alkyl or alkenyl group are converted in a first reaction step to an aldoxime from which in a second reaction step by dehydration, the nitrile is formed.

In NL 105,424 a one step method is described whereby at moderate reaction conditions (reaction temperatures of 20°–40° C. and atmospheric pressure) nitriles are produced from primary alcohols or aldehydes and ammonia in a liquid alkaline medium under the influence of copper compounds.

The aldehydes (or alcohols) which are used as starting material in these known processes have to be prepared in a separate step, preceding the conversion into nitriles. For the preparation of the aldehydes, conventional methods can be applied. Accordingly aliphatic aldehydes with three or more carbon atoms can be obtained from olefins, carbon monoxide and hydrogen under the conditions of the Oxo process, i.e. at moderate reaction temperatures and at relatively high pressures, e.g. of 150 bar and higher (cf "New Syntheses with Carbon Monoxide" by J. Falbe, p. 30,97). It would be advantageous, if nitriles could be prepared directly from olefins at moderate reaction conditions and, of course, without involvement of HCN during the process.

It has now been found that by selecting particular reactants and catalysts, nitriles are directly obtained from the unsaturated compounds used as starting material.

SUMMARY OF THE INVENTION

The invention may be defined as relating to a process for the preparation of nitriles in which an ethylenically or acetylenically unsaturated compound is reacted with carbon monoxide, a hydrogen source and hydroxylamine or a hydroxylamine salt in the presence of a catalyst system comprising one or more Group VIII metals.

DESCRIPTION OF THE PREFERRED EMBODIMENTS

The unsaturated compounds used as starting material in the process according to the invention, may comprise one or more ethylenically and/or acetylenically unsaturated carbon-carbon bonds per molecule.

Preferably, compounds are used whereby the unsaturation mainly or entirely consists in one or more ethylenically unsaturated bonds.

Suitable starting materials include unsaturated hydrocarbons having from 2 to 20 carbon atoms per molecule, preferably from 2 to 8 carbon atoms per molecule.

Typical examples of suitable unsaturated compounds are ethene, propene, n-butenes, isobutene, isomeric pentenes and hexenes, 1-octene, 1-decene, acetylene, phenylacetylene, styrene, cyclopentene and cyclohexene, hexadiene-1,5, cyclooctadiene-1,4 and norbornene.

The unsaturated hydrocarbons may be substituted or unsubstituted. Suitable substituents that do not interfere with the reaction of the invention include dialkylamino-,diarylamino-, cyano-, alkoxy-, aryloxy-, acyl- and alkoxy carbonyl groups.

According to the invention the aforesaid unsaturated compound is reacted with carbon monoxide, a hydrogen source and hydroxylamine or a hydroxylamine salt. Hydroxylamine salts are preferred reactants, in particular salts of hydroxylamine with mineral acids, such as sulfuric acid, sulfonic acid and nitric acid. Hydroxylamine sulfate is in particular preferred.

Carbon monoxide and the hydrogen source, usually hydrogen or a hydrogen rich-gas, may be introduced into the reactor separately, or admixed. They are advantageously supplied in a molar ratio of $CO:H_2$ in the range from about 3:1 to about 1:2 and preferably in the range from about 2:1 to about 1:2. In particular, a substantially equimolar ratio between CO and $H_2$ is preferred.

According to the invention, the reaction is carried out in the presence of a catalyst system comprising at least one Group VIII metal. The Group VIII metals include the noble metals rhodium, ruthenium, palladium, osmium, iridium and platinum and the metals from the iron group: iron, cobalt and nickel.

Catalyst systems containing rhodium and combinations of rhodium and ruthenium are especially preferred.

In the catalyst system, the metals of Group VIII metal may be present in a zero valent form, or as cations. If Group VIII metal cations are present, the system generally comprises one or more anions, such as anions derived from phosphoric acid, nitric acid, methylsulfonic acid or p-toluene-sulfonic acid.

In the zero valent form, the Group VIII metal(s) may be present as metal complex, e.g. with carbonmonoxide.

Preferably, the catalyst system additionally comprises one or more ligands. Suitable ligands are for example ligands containing one or more phosphorus, arsenic and/or nitrogen atoms. Preference is given to phosphorus containing ligands which may be monodentate or multidentate, preferably bidentate. Examples are triphenylphosphine triphenylarsine, $\alpha$, x-alkylidene bisphosphines and pyridine.

A particularly preferred ligand is 1,3-bis(diphenylphosphino)propane.

The number of moles of ligand per gram atom of Group VIII metal is usually in the range from about 0.5 to about 1000, preferably from about 1 to about 50, more preferably from about 2 to about 10.

The number of gram atoms of Group VIII metal per mole of unsaturated compound is not critical. Conveniently the catalyst system is used in an amount such that the number of gram atoms of Group VIII metal per mole of unsaturated carbon-carbon bond is in the range from about $10^{-7}$ to about $10^{-1}$, preferably in the range from about $10^{-6}$ to about $10^{-2}$.

In the event that a catalyst system is used comprising a combination of rhodium and ruthenium the ratio between the number of gram atoms rhodium and ruthenium is preferably in the range from about 1 to about $10^{-3}$, more preferably in the range from about 1 to about $10^{-1}$.

The process according to the invention allows the use of moderate pressures. Conveniently the reaction is carried out at a total pressure in the range from about 2 to about 120 bar, preferably in the range of about 5 to about 100 bar.

Suitable reaction temperatures are in the range from about 80° C. to about 250° C., however, temperatures outside this range are not precluded. Preferred temperatures are in the range from about 100° C. to about 200° C. If desired, the reaction may be performed in the presence of a solvent. Typical examples of suitable solvents are ethers such as diethylether, dimethylether of diethyleneglycol (diglyme) and tetrahydrofuran, alcohols such as hexanol or glycerol, esters such as ethylacetate, ketones such as methylethylketone and methylisobutylketone, and hydrocarbons such as cyclohexane, octane, toluene and the xylenes.

Water, formed in the reaction of the invention, may be conveniently removed by conventional techniques such as Water, formed in the reaction of the invention, may be conveniently removed by conventional techniques such as distillation, in particular azeotropic distillation, or with the aid of a dehydration agent.

Various nitriles obtainable by the process according to the invention are of commercial interest, e.g. as fine chemicals or as intermediates for the production of primary amines which may find use in detergent compositions, as additives or as metal dispersants.

In addition to nitriles, usually significant amounts of alkylhydroxylamines are formed in the reaction. These compounds are easily separated from the reaction mixture and may be used for the preparation of oximes.

The invention will be illustrated by the following Examples which are intended for illustrative purposes and are not to be construed as limiting the scope of the invention. The experiments were performed in a magnetically stirred 250 ml Hastelloy C autoclave (Hastelloy" is a Trade Mark). The reaction mixtures obtained were analysed by means of standard gas-liquid chromatography techniques (GLC).

EXAMPLE 1

50 ml diglyme (dimethylether of diethyleneglycol), 20 ml 1-octene, 7 ml pyridine, 11.5 g hydroxyl-amine sulfate and as catalyst 0.1 mmol rhodium-carbonyl acetylacetonate (Rh(acac)(CO)$_2$)/0.3 mmol 1,3-bis-(diphenylphosphino)propane/2 mmol p-toluenesulfonic acid, were introduced into a magnetically stirred 250 ml Hastelloy C autoclave. The autoclave was pressurized to 50 bar with a 1:1 mixture of carbon monoxide and hydrogen and was then heated to a temperature of 150° C., which temperature was maintained for 5 hours. The contents of the autoclave were then cooled to the ambient temperature. Product analysis by GLC showed a conversion of 1-octene of 89% with a selectivity of 45% to isomeric C$_8$ nitriles and of 50% to isomeric hydroxylamines. The selectivities represent the proportion of a selected product as a percentage of the total amount of converted starting material. The linearity of the nitriles produced was 67%. Only traces of aldehydes could be detected.

EXAMPLE 2

In a similar manner as described in Example 1, an experiment was carried out whereby however as catalyst 0.1 mmol Rh(acac)(CO)$_2$/0.2 mmol ruthenium acetylacetonate (Ru(acac)$_3$)/0.3 mmol-1,3-bis(diphenylphosphino)propane/2mmol p-toluenesulphonic acid was used.

After a reaction period of 5 hours at the conditions as described in Example 1, the reaction mixture was cooled to ambient temperature. Product analysis by GLC showed a conversion of 1-octene of 90 % with a selectivity of 55 % to isomeric C$_8$ nitriles and/of 40 % to isomeric hydroxylamines. The linearity of the nitriles produced was 60%. Traces of aldehydes were found.

EXAMPLE 3

In a similar manner as described in Example 2, an experiment was carried out, whereby however the amount of Rh(acac)(CO)$_2$ in the catalyst was 0.02 mmol instead of 0.1 mmol.

Product analysis by GLC showed that 90% of the 1-octene had been converted with a selectivity of 55% to isomeric C$_8$-nitriles and of 40% to isomeric hydroxylamines. The linearity of the nitriles produced was 72%. Traces of aldehydes were found.

EXAMPLE 4

In a similar manner as described in Example 2, an experiment was carried out, whereby however as catalyst 0.1 mmol Rh(acac) (CO)$_2$/0.2 mmol Ru(acac)$_3$/1,3-bis(diphenylphosphino)propane was used. The catalyst hence did not comprise p-toluenesulphonic acid.

Product analysis by GLC showed that the 1-octene conversion was 90%, the selectivity to isomeric C$_8$-nitriles was 55% and to isomeric hydroxylamines was 40%. The linearity of the nitriles produced wa 65%.

EXAMPLE 5

50 ml diglyme, 20 ml 1-octene, 7 ml pyridine, 11.5 g hydroxylamine-sulfate and as catalyst 0.1 mmol Rh(acac)(CO)$_2$/0.2 mmol Ru(acac)$_3$ were introduced into a magnetic 250 ml Hastelloy C autoclave. The autoclave was pressurized to 60 bar with a 1:2 mixture of carbonmonoxide and hydrogen. The autoclave was heated to a temperature of 130° C., which temperature was maintained for 2 hours. Subsequently the temperature was raised to 150° C. and maintained at that value for 5 hours. The contents of the autoclave were then cooled to ambient temperature. Product analysis by GLC showed that the conversion of 1-octene was 100%, the selectivity to isomeric C$_8$-nitriles was 60%; the selectivity to saturated and monounsaturated hydroxylamines was 35%.

What is claimed is:

1. A process for the preparation of nitriles which comprises reacting at a temperature in the range of from about 100° C. to about 200° C. and a pressure in the range of from about 5 bar to about 100 bar an olefin containing from 2 to 8 carbon atoms with carbon monoxide, hydrogen and hydroxylamine or hydroxylamine-sulfate in the presence of a catalyst system comprising a Group VIII metal selected from the group consisting of rhodium, ruthenium and mixtures thereof.

2. The process as claimed in claim 1, wherein carbon monoxide and the hydrogen are supplied in a molar ratio of $CO:H_2$ in the range of from about 2:1 to about 1:2.

3. The process as claimed in claim 1, wherein said catalyst system further contains a phosphine ligand comprising 1,3-bis(diphenylphosphino)-propane.

4. The process as claimed in claim 3, wherein the number of moles of ligand per gram atom of Group VIII metal is in the range from about 2 to about 10.

5. The process as claimed in claim 1, wherein the reaction is carried out in the presence of an alkaline solvent.

6. A process for the preparation of nitriles which comprises reacting an acetylenically unsaturated compound selected from acetylene or phenylacetylene with carbon monoxide, a hydrogen source and hydroxylamine or a hydroxylamine salt in the presence of a catalyst system comprising at least one Group VIII metal.

* * * * *